(12) United States Patent
Thierry

(10) Patent No.: US 8,772,439 B2
(45) Date of Patent: Jul. 8, 2014

(54) PRODUCTION OF SOLUTIONS OF DIACID/DIAMINE SALTS

(75) Inventor: Jean-François Thierry, Francheville (FR)

(73) Assignee: Rhodia Operations, Aubervilliers (FR)

( * ) Notice: Subject to any disclaimer, the term of this patent is extended or adjusted under 35 U.S.C. 154(b) by 440 days.

(21) Appl. No.: 12/451,851

(22) PCT Filed: May 22, 2008

(86) PCT No.: PCT/EP2008/056328
§ 371 (c)(1), (2), (4) Date: Feb. 25, 2010

(87) PCT Pub. No.: WO2008/148647
PCT Pub. Date: Dec. 11, 2008

(65) Prior Publication Data
US 2010/0168375 A1 Jul. 1, 2010

(30) Foreign Application Priority Data

Jun. 4, 2007 (FR) ..................................... 07 03933

(51) Int. Cl.
*C08G 69/26* (2006.01)

(52) U.S. Cl.
USPC ........... 528/335; 524/590; 528/310; 528/322; 528/336

(58) Field of Classification Search
USPC ........... 528/335, 332, 336, 310, 322; 524/590
See application file for complete search history.

(56) References Cited

U.S. PATENT DOCUMENTS

| | | |
|---|---|---|
| 4,213,884 A | 7/1980 | Eckell et al. |
| 4,233,234 A | 11/1980 | Rotzoll et al. |
| 4,442,260 A | 4/1984 | Larsen |
| 5,801,278 A | 9/1998 | Bletsos et al. |

*Primary Examiner* — Gregory Listvoyb
(74) *Attorney, Agent, or Firm* — Dentons US LLP

(57) ABSTRACT

Solutions of a salt of a diamine and of a diacid, more particularly concentrated solutions of hexamethylene diammonium adipate salt ("nylon salt"), useful starting materials for the production of polyamides, more specifically of PA66, are prepared by mixing a diacid and a diamine, at a salt concentration by weight of from 50% to 80%, in a first stage, to provide aqueous solutions of diacid and diamine having a diacid/diamine molar ratio of greater than 1.1 and, in a second stage, adjusting the diacid/diamine molar ratio, by adding diamine, to a value of from 0.9 to 1.1, preferably from 0.99 to 1.01, and in fixing the salt concentration by weight by, optionally, adding water thereto.

20 Claims, 2 Drawing Sheets

PRODUCTION OF SOLUTIONS OF DIACID/DIAMINE SALTS

CROSS-REFERENCE TO EARLIER APPLICATIONS

Figure 1:
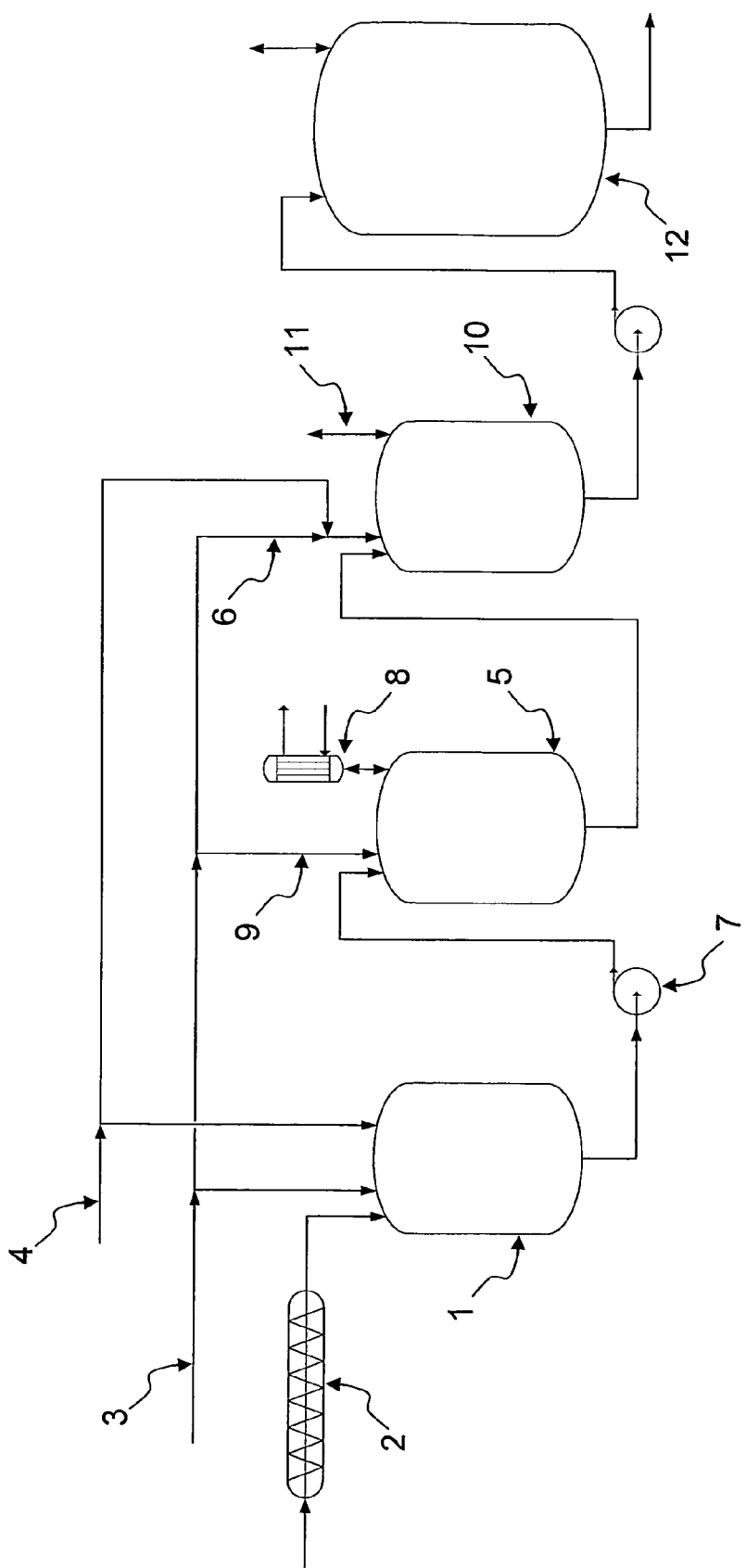

This application is a national phase of PCT/EP 2008/056328, filed May 22, 2008, and designating the United States (published in the French language on Dec. 11, 2008, as WO 2008/148647 A1; the title and abstract were also published in English), which claims foreign priority under 35 U.S.C. §119 of FR 07/03933, filed Jun. 4, 2007, each hereby expressly incorporated by reference in its entirety and each assigned to the assignee hereof.

The present invention relates to a process for the manufacture of a solution of a salt of a diamine and of a diacid for the manufacture of polyamide.

More particularly, the invention relates to a process for the manufacture of a concentrated solution of hexamethylene diammonium adipate salt, also called nylon salt, used as starting material for the manufacture of polyamide, more specifically of PA66.

In order to obtain polyamides comprising diacid and diamine monomers of high molecular weight, an aqueous solution of a salt formed by reaction between a diamine molecule and a diacid molecule is generally used. This solution is heated in order to initially evaporate off the water and then in order to initiate the polymerization by polycondensation, so as to obtain macromolecular chains comprising amide functions.

The salt solution generally contains stoichiometric amounts of diacids and diamines. The concentration by weight of nylon salt is generally between 50% and 65%. This solution is generally stored before being transported, where appropriate, then fed into polymerization installations.

The maximum admissible concentration of nylon salt in order to avoid problems of precipitation is of the order of 70% by weight at atmospheric pressure. Above this concentration, it is necessary to heat the solution at temperatures between 110 and 160° C., at a pressure higher than atmospheric pressure, in order to prevent any precipitation. These temperature and pressure ranges are not easily compatible with storage and transport.

Several processes for manufacturing a nylon salt solution have been proposed. These processes generally consist in adding adipic acid to hexamethylene diamine and water, while evacuating the heat produced by the neutralization reaction.

Thus, U.S. Pat. No. 4,233,234 describes a process for the manufacture of a hexamethylene diammonium adipate comprising a mixing reactor and circulation of the solution in a mixing zone, and then in a cooler in order to evacuate the heat generated by the reaction between the diacid and the diamine.

U.S. Pat. No. 4,442,260 describes a process consisting of producing an aqueous solution containing from 31% to 40% of water, 73.5% to 77.5% of adipic acid and 22.5% to 26.5% of hexamethylene diamine, and then in evaporating a large amount of the water in order to obtain a nonstoichiometric salt concentration by weight of 89% to 96%, and adding hexamethylene diamine in order to obtain a stoichiometric diacid/diamine ratio equal to 1.

These various manufacturing processes require, firstly, the input of heat in order in particular to dissolve the adipic acid and, secondly, evacuation of the heat generated by the reaction between the amine and the acid, and also require the water to be evaporated off.

One of the objectives of the present invention is to propose a process for preparing a concentrated solution of nylon salt or salt of a diacid and of a diamine, using the minimum energy exchange with the exterior, i.e. minimizing the input and evacuation of heat.

To this effect, the invention proposes a process for the manufacture of an aqueous solution of salts of diamines and diacids, obtained by mixing a diacid and a diamine, at a salt concentration by weight of between 50% and 80%, characterized in that it consists in:
producing, in a first reactor, an aqueous solution of diamine and diacid with a diacid/diamine molar ratio of between 1.5 and 5 and a concentration of the dissolved species in water of between 40% and 75% by weight, preferably 45% and 65%, by feeding into said reactor containing either at least 5% by volume of aqueous solution of diamine and diacid with a molar ratio of between 1.5 and 5, or water representing at least 10% of the total amount of water to be fed into said reactor, a stream comprising diacid, a stream comprising diamine and, optionally, a stream of water at the temperature $T_1$, the flow rates of the feed stream comprising diacid and of the feed stream comprising diamine being controlled so that the temperature of the solution in the reactor is constantly below the boiling point at the operating pressure of said reactor and so that the diacid/diamine molar ratio is constantly greater than 1.1, the amount of acid fed corresponding to at least 90% by weight of the total mass of the acid required to produce the desired amount of aqueous salt solution, the amount of water fed representing at least 75% by weight of the total mass of water required to produce the desired amount of the aqueous salt solution;
transferring the aqueous solution obtained in the first reactor into a second reactor equipped with a condenser;
feeding into the second reactor a stream comprising diamine so as to obtain a diacid/diamine molar ratio of between 0.9 and 1.1, preferably between 1.0 and 1.05, the solution being brought to a temperature at most equal to the boiling point of the solution at the operating pressure by means of at least the release of heat from the reaction between the diamine and the diacid, and, optionally, feeding the amounts of additional water and/or diacid so as to obtain the salt solution at the desired concentration and with the desired diacid/diamine ratio.

The term "dissolved species" should be understood to mean all the diacid and diamine species present in the medium in free form or salt form, or the like.

The term "boiling point" should be understood to mean the boiling point of the solution contained in a reactor at the working or operating pressure of the process.

As diamines that are suitable for the invention, mention may be made of hexamethylene diamine (HMD) as preferred and most commonly used monomer, and also heptamethylene diamine, tetramethylene diamine, octamethylene diamine, nonamethylene diamine, decamethylene diamine, 2-methylpentamethylene diamine, undecamethylene diamine, dodecamethylene diamine, xylylene diamine and isophorone diamine. A mixture of several diamines monomers can be used.

In the process of the invention, the diamine is fed in pure form, or preferably in the form of a concentrated aqueous solution. For HMD, a solution comprising at least 50% by weight of diamine, preferably at least 85%, and even more advantageously 90% by weight approximately is preferably used. However, the stream comprising the diamine may contain other compounds, without nevertheless departing from the context of the invention.

As diacids that are suitable for the invention, mention may be made of suberic acid, sebacic acid, dodecanedioic acid, isophthalic acid, terephthalic acid, azelaic acid, pimelic acid and naphthalenedicarboxylic acid, for example. A mixture of several diacids monomers can be used. Adipic acid is the monomer which is preferred and most commonly used. It is used in powdered form. However, it may also be fed into the reactor in the form of an aqueous solution or a suspension.

As for the stream comprising the diamine, the stream comprising the diacid may contain other compounds and/or solvents, without nevertheless departing from the context of the invention.

In addition, the streams of products fed into the first reactor may preferably be distinct. However, the diamine may be added with the water and part of the diacid. Similarly, the diacid is preferably fed in powdered form. However, it may be fed in the form of an aqueous solution or dispersion or in dissolved form, for example, in an aqueous solution of diamine/diacid salt, without nevertheless departing from the context of the invention.

The process of the invention is advantageously carried out while maintaining the various reactors, more particularly the second and third reactors as described herebelow, under an oxygen-free atmosphere, for instance under an atmosphere composed of nitrogen, rare gases, steam or a mixture thereof.

In a preferred embodiment, the oxygen-free atmosphere is obtained either by continuous feeding with a stream of nitrogen, or by maintaining a nitrogen pressure in the various reactors and by generating steam by boiling the solution.

In the latter case, it is advantageous for the nitrogen to be evacuated or allowed to escape through a condenser mounted on the reactor. Thus, the water carried over with the nitrogen is condensed and recycled into the reactor.

This embodiment also makes it possible to evacuate the oxygen present, for example in dissolved form, in the solution and therefore prevents oxidation of the monomers, in particular of the diamine. The oxygen may be introduced, in particular, by the diacid monomer, more preferably when a powder of diacid monomer is fed.

In another embodiment, the dissolved oxygen is evacuated by steam distillation using the steam generated by the boiling of the solution in the second reactor, when the temperature of the solution is equal to this boiling point.

The process of the invention can be carried out according to a batch mode or a continuous mode. These two embodiments are described in detail below.

The process of the invention can be carried out in any type of reactor. More particularly, the reactors comprise mechanical agitation and may be equipped with means for keeping them at temperature, in particular during periods when they are not running or periods when the manufacturing programme is being changed.

In the batch-mode embodiment, the process of the invention is preferably carried out in an installation comprising several reactors mounted in series, each reactor corresponding to the performing of one step of the process. However, without departing from the context of the invention, the various steps of the process may be carried out successively in the same reactor. Similarly, the installation may comprise several reactors mounted in parallel, for carrying out one step of the process.

The concentrated salt solution obtained according to the process of the invention may be fed directly and continuously into a polymerization installation, or may be stored before transfer and use.

Figure 2:
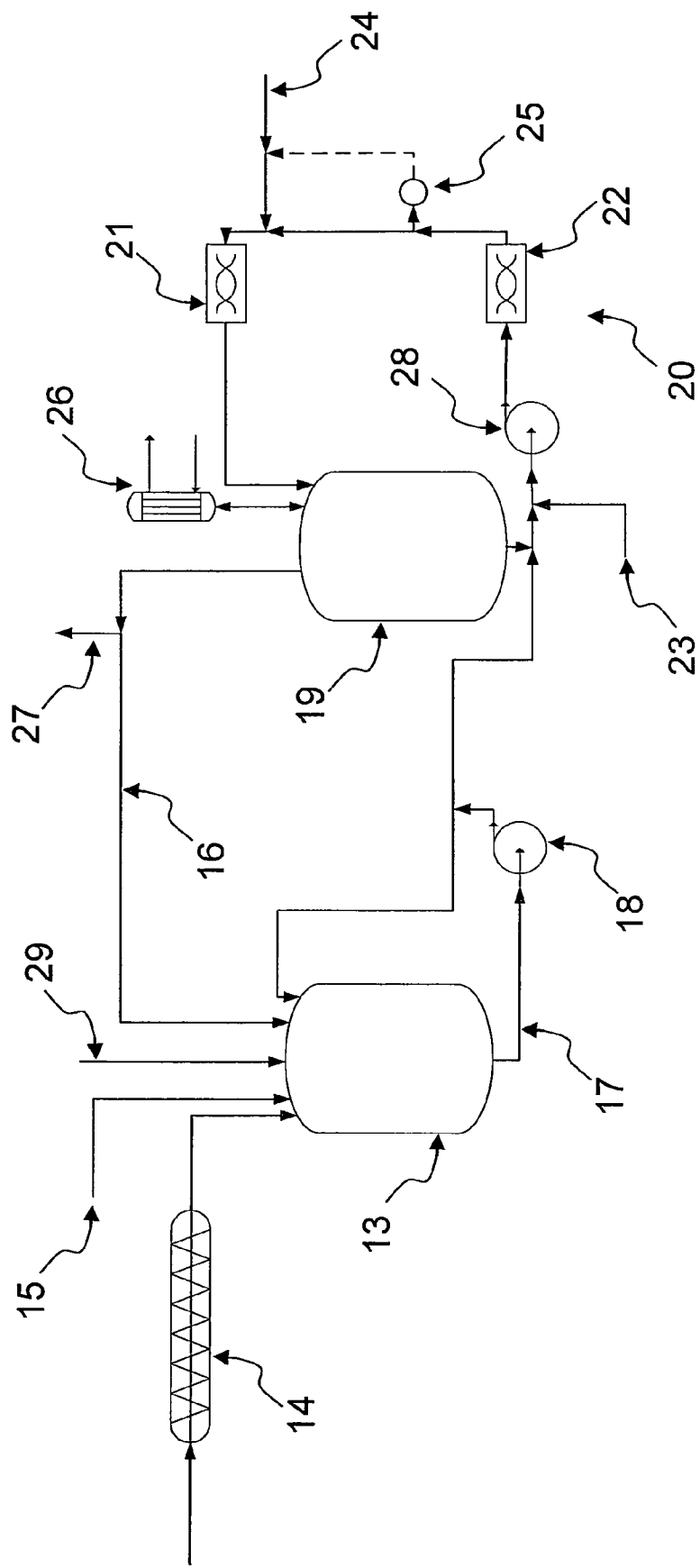

A detailed description of two embodiments of the process of the invention is given below with reference to the attached FIGS. 1 and 2 in which:

FIG. 1 represents a synoptic scheme of an installation for carrying out the process according to a batch-mode embodiment, and FIG. 2 represents a synoptic scheme of an installation for carrying out the process according to a continuous-mode embodiment.

The invention is also illustrated by the examples of the manufacture of concentrated solutions of nylon salt obtained according to the batch-mode embodiment of the process.

In the description below, the terms adipic acid (AA) and hexamethylene diamine (HMD) will be used to denote the diacid and the diamine. However, this process also applies to other diacids and other diamines indicated above.

With reference to FIG. 1, this figure describes a first embodiment of the process of the invention operating according to the batch mode. The installation comprises a stirred first reactor 1, in which adipic acid 2, generally in the form of a powder, and a liquid stream 3 of hexamethylene diamine are added. Water 4 is also introduced into this reactor.

The hexamethylene diamine is advantageously a concentrated aqueous solution comprising 90% by weight of HMD.

The various products are added in reactor 1, which contains a small amount of solution of adipic acid and of hexamethylene diamine in water, rich in adipic acid, and called starter solution. This aqueous solution is advantageously a small portion of the solution prepared in a prior operation and advantageously has a composition that is substantially the final composition of the solution that will be prepared in this reactor 1, i.e. a diacid/diamine molar ratio equal to approximately 2.4 and a concentration by weight of dissolved species of approximately 57%.

The amount of solution present in the reactor at the beginning of the step is equal to at least approximately 5%, preferably between 5% and 40%, preferentially between 10% and 35% of the total amount of solution produced in reactor 1, at the end of the step.

Advantageously, according to one feature of the invention, no heat exchange is carried out between the reactor and the environment, or the exterior, i.e. this reactor operates in quasi-adiabatic mode.

The temperature in reactor 1 increases slightly due to the neutralization reaction between the HMD and the adipic acid. However, the temperature of the solution in the reactor, throughout the process and at the end of the step, will always be at a low temperature, advantageously below 100° C., preferably below 75° C., and more generally below the boiling point of the solution at the operating pressure. This low temperature level is advantageous for limiting oxidation of the HMD by the oxygen present in the medium. This oxygen may in particular be introduced by the adipic acid powder.

When the amounts of water, adipic acid and HMD required to obtain an aqueous solution containing adipic acid, and diacid and diamine salt with an overall diacid/diamine molar ratio equal to 2.4 and a concentration by weight of dissolved species of 57% are fed into the reactor. When the volume of the liquid in the reactor advantageously represents at least 80% of the working volume of reactor 1, the solution is fed into a second reactor 5, called neutralization reactor, by means of a pump 7. This reactor 5 is equipped with a condenser 8 and advantageously with an external loop for circulating the solution and/or with a stirring device (not represented).

Hexamethylene diamine 9 is fed into this second reactor 5 in order to obtain an AA/HMD molar ratio in the region of 1.01. As for the first reactor 1, no significant heat exchange is advantageously performed with the exterior. Thus, the heat from the reaction in which the amine is neutralized by the acid causes an increase in the temperature in the reactor 5, this temperature reaching at most the boiling point of the mixture at the operating pressure. The water which evaporates off is condensed in the condenser 8 so as to obtain total reflux of the water. This temperature characteristic to obtain boiling is advantageous since it makes it possible to eliminate, by steam distillation, the oxygen present in the medium, in particular in dissolved form. The heat exchange performed in this condenser is very low and represents only a very small part of the heat given off by the neutralization reaction.

Water can also be added in order to adjust the concentration of hexamethylene ammonium adipate salt to a concentration by weight of greater than 50%, preferably between 60% and 75% by weight. The water may advantageously be mixed with the stream of hexamethylene diamine.

In the embodiment illustrated, which is the preferred embodiment of the invention, the solution obtained in the second reactor 5 is fed into a third reactor 10 equipped with a stirring device or of an external loop of circulation of reaction medium (not represented) and advantageously with a condenser 11.

This third reactor 10, also called adjustment reactor, is analogous in terms of its principle to the second reactor and comprises an addition 6 of HMD and of water in order to adjust the AA/HMD ratio to a value of between 0.995 and 1.005, and to adjust, if necessary, the concentration of salt to the desired value.

The solution thus obtained can be used directly in a polymerization installation or can be stored in a storage tank 12 or in containers suitable for transport.

According to a preferred embodiment, the reactors of the installation are maintained under an oxygen-free atmosphere by feeding, for example, nitrogen into the empty reactor and maintaining this nitrogen atmosphere during filling and draining of the reactors. The nitrogen feeds for each reactor are not represented on the attached figure.

Advantageously, the reactors are equipped with thermal insulation in order to limit heat exchanges with the outside environment and thus to limit heat losses.

In this embodiment, the dissolved oxygen will be evacuated by being carried over with the nitrogen which escapes from the reactor during the filling thereof. This evacuation of the nitrogen is preferably carried out through a condenser so as to thus condense the steam carried over by the nitrogen.

With reference to FIG. 2, a second embodiment of the process of the invention is described. This second embodiment relates to a process operating according to a continuous mode. As in the first embodiment, the process comprises a first step of dissolution of the adipic acid carried out in the reactor 13. The adipic acid is fed by means of an endless screw system 14, simultaneously with water 15 and with a stream 16 of concentrated nylon salt solution, so as to obtain in the reactor 13 a solution containing a diacid/diamine molar ratio of between 1.5 and 5, preferably in the region of 2.4, and a concentration by weight of dissolved species of between 40% and 75%, for example equal to 57%. In another embodiment, the diamine is fed into the reactor 13 by means of a stream that is independent of the stream of concentrated salt solution, it being possible for the total diamine feed into the reactor 13 to be obtained either by means of the diamine feed alone, or by means of the stream of concentrated salt solution, or alternatively by means of the addition of these two streams.

In order to obtain homogenization of the solution in the reactor 13, an external circulation loop 17 comprising a pump 18 is illustrated. A part of the solution circulating in the loop feeds a reactor 19 also equipped with an external neutralization loop 20 comprising a pump 28 and two static mixers 21 and 22. Upstream of each mixer is an HMD feed 23 and a monomer feed 24 for adjusting the diacid/diamine molar ratio to a value of between 0.99 and 1.01.

This molar ratio is advantageously controlled and adjusted by means of the device 25 for measuring the pH of the solution and the addition of additional diamine and/or diacid downstream of the measurement of the pH. As in the first embodiment, the heat given off by the neutralization allows the temperature of the solution to increase, until at most the boiling point of the solution at the operating pressure is reached.

In order to condense the water thus evaporated off, a condenser 26 is provided for on the reactor 19.

In the embodiment illustrated, part of the solution produced in the reactor 19 is sent to the first reactor 13 via the pipe 16, the other part 27 is directed to storage tanks that are not represented.

It is possible not to recycle the concentrated salt solution into the first reactor. In this case, the diamine is introduced into the first reactor by means of a distinct feed 29, in pure form or in the form of an aqueous solution. The two diamine feeds 16 and 29 into the first reactor may be present simultaneously.

The examples below illustrate more clearly the process of the invention and the characteristics and advantages thereof.

EXAMPLE 1

Production of an Aqueous Solution of Nylon Salt at 62% by Weight, According to the Batch Process Stage 1—Dissolution of Adipic Acid An aqueous solution of adipic acid and hexamethylene diamine is prepared by adding powdered adipic acid (35.0 kg) and hexamethylene diamine (12.9 kg of an aqueous solution at 90% by weight at a temperature of 45° C.) into the thermally insulated reactor 1, containing an aqueous solution obtained by adding water (34.4 kg; at a temperature of 40° C.) to a starter of 14 kg of aqueous solution of adipic acid and hexamethylene diamine having an AA/HMD=2.4, at a temperature of 63° C. and a concentration by weight of dissolved species of 56.6%.

This starter solution is a small part of the solution obtained in the reactor 1 in the previous manufacturing process. The adipic acid and the HMD are added simultaneously, taking care to ensure that there is always an excess of acid in the mixture (AA/HMD molar ratio greater than 1.1). The homogeneity of the solution is ensured by mechanical stirring. At the end of the first stage, the dissolved species (56.6% by weight) consist of 75.1% by weight of adipic acid and 24.9% by weight of hexamethylene diamine. The final temperature of the solution is 63° C.

Stage 2—Neutralization 82.3 kg (i.e. approximately 85.5%) of the solution obtained in stage 1 are transferred into the reactor 5 of FIG. 1, which is thermally insulated and equipped with a condenser 8. Part of the solution obtained is conserved as starter solution in the reactor 1 for a subsequent operation.

17.5 kg of an aqueous solution of hexamethylene diamine containing 90% by weight of HMD and at a temperature of 45° C. are added into the reactor 5 in order to obtain an aqueous solution of nylon salt, the diacid/diamine ratio of which is close to stoichiometry (AA/HMD molar ratio=1.017).

The energy or heat given off by the neutralization reaction causes the temperature of the medium to increase to the boiling point, i.e. 108° C. in the example described. The vapours produced are condensed in the condenser 8 and form a total reflux in the reactor 5. The energy evacuated by the condensation of the vapours corresponds to the excess neutralization energy. Thus, the process makes it possible to maintain the system at the temperature of 108° C. (beginning of boiling at atmospheric pressure), without requiring the use of means for evacuating the heat generated by the neutralization reaction.

Stage 3—Finishing

The concentration and the pH of the solution are then adjusted by adding 0.9 kg of water at a temperature of 40° C. and 0.43 kg of an aqueous solution of HMD at 90% by weight and at a temperature of 45° C., after transfer of the solution into a third reactor. At the end of this stage, the solution is an aqueous solution containing 62.0% by weight of nylon salt with an adipic acid/HMD molar ratio equal to 1.003 and a pH equal to 7.21. The pH is measured at 20° C. on a sample of the solution diluted with water, so as to obtain a concentration of dissolved species equal to 100 g/l.

The solution obtained is then stored in a tank 12 illustrated in FIG. 1.

EXAMPLE 2

Production of Nylon Salt at 68% According to the Batch Process

Stage 1—Dissolution of Adipic Acid

An aqueous solution of adipic acid and hexamethylene diamine is prepared by adding 38.0 kg of powdered adipic acid and 14.0 kg of an aqueous solution of hexamethylene diamine containing 90% by weight of HMD and at a temperature of 45° C., into the reactor 1 containing an aqueous solution obtained by adding 27.7 kg of water, at a temperature of 40° C., to a starter of 14 kg of aqueous solution of adipic acid and hexamethylene diamine having an AA/HMD molar ratio=2.4, at a temperature of 68° C., and a concentration by weight of dissolved species of 63.5%.

This starter solution is a small part of the solution obtained in the reactor 1 in the preceding manufacturing operation. The adipic acid and the HMD are added simultaneously, taking care to ensure that there is always an excess of acid in the mixture (AA/HMD molar ratio greater than 1.1). The homogeneity of the solution is ensured by mechanical stirring. At the end of the first stage, the dissolved species (63.5% by weight) consist of 75.1% by weight of adipic acid and 24.9% by weight of hexamethylene diamine. The final temperature of the solution is 68° C.

Stage 2—Neutralization 79.7 kg (i.e. approximately 85%) of the solution obtained in stage 1 are transferred into the reactor 5 of FIG. 1, equipped with a condenser 8. A part of the solution obtained is conserved as starter solution in the reactor 1 for a subsequent operation.

19.0 kg of an aqueous solution of hexamethylene diamine containing 90% by weight of HMD and at a temperature of 45° C. are added into the reactor 5 so as to obtain an aqueous solution of nylon salt, the diacid/diamine ratio of which is close to stoichiometry (AA/HMD molar ratio=1.017).

The energy or heat given off by the neutralization reaction causes the temperature of the medium to increase up to the boiling point, i.e. 110° C. in the example described. The vapours produced are condensed in the condenser 8 and form a total reflux in the reactor 5. The energy evacuated by the condensation of the vapours corresponds to the excess neutralization energy. Thus, the process makes it possible to maintain the system at the temperature of 110° C. (beginning of boiling at atmospheric pressure).

Stage 3—Finishing

The concentration and the pH of the solution are then adjusted by adding 1.0 kg of water at a temperature of 40° C. and 0.47 kg of an aqueous solution of HMD at 90% by weight of HMD and at a temperature of 45° C., after transfer of the solution into a third reactor 10 equipped with a condenser 11. At the end of this stage, the solution is an aqueous solution containing 68.0% by weight of nylon salt with an AA/HMD molar ratio equal to 1.003.

The invention claimed is:

1. A process for the production of an aqueous solution of salts of diamines and diacids, comprising:
    (a) producing an aqueous solution of diamine and diacid having a diacid/diamine molar ratio from 1.5 to 5 and a concentration of dissolved reactants comprising diamine and diacid in water from 40% to 75% by weight, in a first reaction zone containing either (i) at least 5% by volume of aqueous solution of diamine and diacid with a molar ratio ranging from 1.5 to 5, or (ii) water constituting at least 10% of the total amount of water to be introduced into said reaction zone, a stream comprising diacid, by feeding into said reaction zone a stream comprising diamine and, optionally, a stream of water, the flow rates of the feed stream comprising diacid and of the feed stream comprising diamine being controlled such that the temperature of the solution in said reaction zone is constantly below the boiling point at the operating pressure in said reaction zone and such that the diacid/diamine molar ratio is constantly greater than 1.1, the amount of acid introduced corresponding to at least 90% by weight of the total mass of the acid required to produce the desired amount of aqueous salt solution, the amount of water introduced constituting at least 75% by weight of the total mass of water required to produce the desired amount of the aqueous salt solution;
    (b) transferring the aqueous solution obtained in the first reaction zone into a second reaction zone equipped with a condenser; and
    (c) introducing into the second reaction zone a stream comprising diamine to provide a diacid/diamine molar ratio ranging from 0.9 to 1.1, the temperature of the solution being adjusted to at most 110° C. and, optionally, introducing amounts of additional water and/or diacid such as to provide the salt solution with the desired concentration and with the desired diacid/diamine ratio,
    thereby, obtaining an aqueous solution of salts of diamines and diacids at a salt concentration ranging from 50% to 80% by weight.

2. The process as defined by claim 1, wherein the concentration of dissolved reactants in the first reaction zone ranges from 45% to 65% by weight.

3. The process as defined by claim 1, wherein the diacid/diamine molar ratio in the second reaction zone ranges from 1.00 to 1.05.

4. The process as defined by claim 1, wherein the solution obtained in the second reaction zone is transferred into a third reaction zone, optionally maintained in the absence of oxygen, equipped with a condenser, into which are added a stream comprising diamine and/or a stream comprising diacid and, optionally, a stream of water such as to adjust the diacid/diamine ratio to 0.99 to 1.01 and to adjust the concentration by weight of salt.

5. The process as defined by claim 4, wherein at least the second and third reaction zones are maintained under an oxygen-free atmosphere.

6. The process as defined by claim 4, wherein at least the second and third reaction zones are under an oxygen-free atmosphere comprising nitrogen, a rare gas, steam or a mixture thereof.

7. The process as defined by claim 1, carried out in batch mode.

8. The process as defined by claim 7, wherein the aqueous solution forming the aqueous beginning solution constitutes at least 5% by volume of the desired amount of solution produced in said reaction zone at the end of the first stage.

9. The process as defined by claim 8, wherein the aqueous solution forming the aqueous beginning solution constitutes from 5% to 40% by weight of the desired amount of solution produced in said reaction zone at the end of the first stage.

10. The process as defined by claim 1, wherein the temperature in the second reaction zone is at most equal to the boiling point of the solution at the operating pressure, the condenser generating a reflux of condensed water.

11. The process as defined by claim 4, wherein the temperature in the third reaction zone is at most equal to the boiling point of the solution at the operating pressure, the condenser generating a reflux of condensed water.

12. The process as defined by claim 1, wherein the stream comprising diamine introduced into the first reaction zone comprises an aqueous solution of diamine.

13. The process as defined by claim 12, wherein the concentration of diamine in the said aqueous solution is at least 50% by weight.

14. The process as defined by claim 1, carried out in continuous mode.

15. The process as defined by claim 14, wherein the stream comprising diamine introduced into the first reaction zone at least partially comprises the concentrated salt solution produced thereby.

16. The process as defined by claim 14, wherein the second reaction zone comprises an external circulation loop including at least one static mixer.

17. The process as defined by claim 16, wherein an inlet of the stream comprising diamine into the second reaction zone is located upstream of the static mixer.

18. The process as defined by claim 17, wherein the inlet of the stream of salt solution originating from the first reaction zone is located upstream of the diamine feed.

19. The process as defined by claim 16, wherein means for measuring the pH of the solution is located downstream of the static mixer, and the diacid/diamine molar ratio is adjusted by introducing a stream of diamine and/or of diacid, downstream of a point at which the pH is measured and as a function of such measurement.

20. The process as defined by claim 1, wherein the diamine comprises hexamethylene diamine and the diacid comprises adipic acid.

\* \* \* \* \*